United States Patent
Ludwig et al.

(10) Patent No.: US 9,180,227 B2
(45) Date of Patent: Nov. 10, 2015

(54) COATING LAYERS FOR MEDICAL DEVICES AND METHOD OF MAKING THE SAME

(71) Applicant: Abbott Cardiovascular Systems Inc., Santa Clara, CA (US)

(72) Inventors: Florian N. Ludwig, Hilversum (NL); Syed F. A. Hossainy, Hayward, CA (US); Srinivasan Sridharan, Mendham, NJ (US); Carol Lee, Sunnyvale, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 14/053,796

(22) Filed: Oct. 15, 2013

(65) Prior Publication Data
US 2014/0037832 A1   Feb. 6, 2014

Related U.S. Application Data

(62) Division of application No. 11/445,041, filed on May 31, 2006, now Pat. No. 8,568,764.

(51) Int. Cl.
| | |
|---|---|
| *A61L 27/54* | (2006.01) |
| *A61L 27/34* | (2006.01) |
| *A61L 31/10* | (2006.01) |
| *A61L 27/50* | (2006.01) |
| *A61M 31/00* | (2006.01) |

(52) U.S. Cl.
CPC .............. *A61L 31/10* (2013.01); *A61L 27/34* (2013.01); *A61L 27/50* (2013.01); *A61L 27/54* (2013.01); *A61M 31/002* (2013.01); *A61L 2300/406* (2013.01); *A61L 2300/41* (2013.01); *A61L 2300/416* (2013.01); *A61L 2300/606* (2013.01)

(58) Field of Classification Search
CPC .............................. B05D 3/046; A61L 27/3687
See application file for complete search history.

(56) References Cited

U.S. PATENT DOCUMENTS

| | | |
|---|---|---|
| 4,733,665 A | 3/1988 | Palmaz |
| 4,800,882 A | 1/1989 | Gianturco |
| 4,886,062 A | 12/1989 | Wiktor |
| 6,509,040 B1 | 1/2003 | Murray et al. |
| 6,562,374 B1 | 5/2003 | Han et al. |
| 6,620,356 B1 * | 9/2003 | Wong et al. .................... 264/41 |
| 6,627,246 B2 | 9/2003 | Mehta et al. |
| 6,908,624 B2 | 6/2005 | Hossainy et al. |
| 7,323,209 B1 | 1/2008 | Esbeck et al. |
| 8,048,442 B1 | 11/2011 | Hossainy et al. |
| 8,246,973 B2 | 8/2012 | Hossainy et al. |
| 8,252,361 B2 | 8/2012 | Kramer-Brown et al. |
| 8,293,318 B1 | 10/2012 | Hsu et al. |
| 8,377,107 B2 | 2/2013 | Kleiner et al. |
| 8,377,499 B2 | 2/2013 | Kleiner et al. |
| 8,389,044 B2 | 3/2013 | Kleiner et al. |
| 8,551,512 B2 | 10/2013 | Hossainy et al. |
| 8,568,764 B2 | 10/2013 | Ludwig et al. |
| 8,715,707 B2 | 5/2014 | Hossainy et al. |
| 8,828,418 B2 | 9/2014 | Ludwig et al. |
| 2001/0053753 A1 | 12/2001 | Engekhart |
| 2002/0032477 A1 | 3/2002 | Helmus et al. |
| 2002/0091437 A1 | 7/2002 | Tseng et al. |
| 2003/0074049 A1 | 4/2003 | Hoganson et al. |
| 2003/0083740 A1 * | 5/2003 | Pathak .......................... 623/1.43 |
| 2003/0203991 A1 | 10/2003 | Schottman et al. |
| 2004/0039441 A1 | 2/2004 | Rowland et al. |
| 2004/0072922 A1 | 4/2004 | Hossainy et al. |
| 2004/0091603 A1 * | 5/2004 | Priewe .......................... 427/2.24 |
| 2004/0102558 A1 | 5/2004 | Lin et al. |
| 2004/0138695 A1 | 7/2004 | Li et al. |
| 2004/0177805 A1 | 9/2004 | Hijlkema et al. |
| 2004/0199241 A1 | 10/2004 | Gravett et al. |
| 2004/0220665 A1 | 11/2004 | Hossainy et al. |
| 2004/0261698 A1 | 12/2004 | Roorda et al. |
| 2005/0038504 A1 | 2/2005 | Halleriet et al. |
| 2005/0070997 A1 | 3/2005 | Thornton et al. |
| 2005/0109158 A1 | 5/2005 | Keener |
| 2005/0131201 A1 | 6/2005 | Pacetti et al. |
| 2005/0132466 A1 | 6/2005 | Janssen et al. |
| 2005/0154450 A1 | 7/2005 | Larson et al. |
| 2005/0191332 A1 | 9/2005 | Hossainy |
| 2005/0196518 A1 * | 9/2005 | Stenzel .......................... 427/2.1 |
| 2005/0255230 A1 | 11/2005 | Clerc et al. |

(Continued)

FOREIGN PATENT DOCUMENTS

| | | |
|---|---|---|
| EP | 1 518 570 A1 | 3/2005 |
| JP | 2002-345972 A | 12/2002 |
| WO | WO 01/52915 A1 | 7/2001 |
| WO | WO 2004/087214 A1 | 10/2004 |
| WO | WO 2004/112863 A1 | 12/2004 |

OTHER PUBLICATIONS

"Common Organic Solvents:Table of Properties" retrieved online from Northern Ohio University, Dept of Organic Chemistry (p. 1-3) Nov. 24, 2009.*

(Continued)

*Primary Examiner* — H. Sarah Park

(74) *Attorney, Agent, or Firm* — Squire Patton Boggs (US) LLP

(57) ABSTRACT

Methods are disclosed for controlling the morphology and the release-rate of active agent from coating layers for medical devices comprising a polymer matrix and one or more active agents. The methods comprise fixing the morphology or phase distribution of the active agent prior to removing solvent from the coating composition. The coating layers can be used for controlled the delivery of an active agent or a combination of active agents.

19 Claims, 1 Drawing Sheet

(56) References Cited

U.S. PATENT DOCUMENTS

| | | | |
|---|---|---|---|
| 2005/0271701 A1 | 12/2005 | Cottone et al. | |
| 2005/0288481 A1* | 12/2005 | DesNoyer et al. | 528/310 |
| 2006/0035011 A1* | 2/2006 | Stenzel | 427/2.1 |
| 2006/0196073 A1 | 9/2006 | Parker | |
| 2006/0246109 A1 | 11/2006 | Hossainy et al. | |
| 2007/0154512 A1* | 7/2007 | Dave et al. | 424/423 |
| 2007/0202323 A1 | 8/2007 | Kleiner et al. | |
| 2007/0286882 A1 | 12/2007 | Tang et al. | |
| 2008/0095918 A1 | 4/2008 | Kleiner et al. | |
| 2008/0124372 A1 | 5/2008 | Hossainy et al. | |
| 2009/0326645 A1 | 12/2009 | Pacetti et al. | |
| 2011/0086162 A1 | 4/2011 | Hossainy et al. | |
| 2011/0144741 A1 | 6/2011 | Kleiner et al. | |
| 2014/0037831 A1 | 2/2014 | Ludwig et al. | |

OTHER PUBLICATIONS

"1,1,1-trichloroethane" Wikipedia (http://en.wikipedia.org/wiki/1,1,1-Trichloroethane) retrieved online on Dec. 18, 2013, p. 1, "properties" Table.*

"Dimethyl acetamide" Wikipedia (http://en.wikipedia.org/wiki/Dimethylacetamide) retrieved online on Dec. 18, 2013, p. 1.*

"2,2,4-Trimethylpentane" Wikipedia (http://en.wikipedia.org/wiki/2,2,4-Trimethylpentane) retrieved online on Dec. 18, 2013, p. 1-2.*

Nordestgaard et al., Critical-point drying versus freeze drying for scanning electron microscopy: a quantitative and qualitative study on isolated hepatocytes (1985) *J Microsc.* 137:189-207, one-page abstract only.

Critical Point Drying Principles, Electron Microscopy Sciences catalog, https://www.emsdiasum/com/microscopy/technical/datasheet/critical_drying.aspx, printed on Jun. 27, 2014.

Freeze-drying, Wikipedia, http://en.wikipedia.org/wiki/Freeze-drying, last modified on Jun. 2, 2014, printed on Jun. 27, 2014, 8 pages.

International Search Report for PCT/US2007/009114, filed Apr. 13, 2007, mailed Jan. 29, 2008, 16 pgs.

Anonymous, *Cardiologists Draw—Up the Dream Stent*, Clinica 710:15 (Jun. 17, 1996), http://www.dialogweb.com/cgi/document?req=1061848202959, printed Aug. 25, 2003 (2 pages).

Anonymous, Critical Point Drying Principles, http://www.emsdiasum.com/microscopy/technical/datasheet/critical-drying, printed Mar. 20, 2014, 6 pages.

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Herdeg et al., *Antiproliferative Stent Coatings: Taxol and Related Compounds*, Semin. Intervent. Cardiol. 3:197-199 (1998).

Kell, Low Temperature Bath (1960) *Journal of Applied Polymer Science* IV:252.

Kuribayashi et al. Self-deployable origami stent grafts as a biomedical application of Ni-rich TiNi shape memory alloy foil (2006) *Materials Science Engineering A* 419:131-137.

Levy et al., *Strategies for Treating Arterial Restenosis Using Polymeric Controlled Release Implants*, Biotechnol. Bioact. Polym. [Proc. Am. Chem. Soc. Symp.], pp. 259-268 (1994).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, EPO Heart Journal 14, p. 321 (P1694), Abstr. Suppl. (1993).

Ozaki et al., *New Stent Technologies*, Progress in Cardiovascular Diseases, vol. XXXIX(2):129-140 (Sep./Oct. 1996).

Peng et al., *Role of polymers in improving the results of stenting in coronary arteries*, Biomaterials 17:685-694 (1996).

Van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

"Supercritical and Critical Point Drying," http://apeksfab.com/Critical_Point_Drying.html, printed Oct. 25, 2014.

"Supercritial Fluid Extraction (SFE) Systems: Waters," http://www.waters.com/waters/en_US/Supercritical-Fluid-Extraction-(SFE)-Systems/ nav.htm?cid=10146521&locale=en_US, printed Oct. 25, 2014.

* cited by examiner

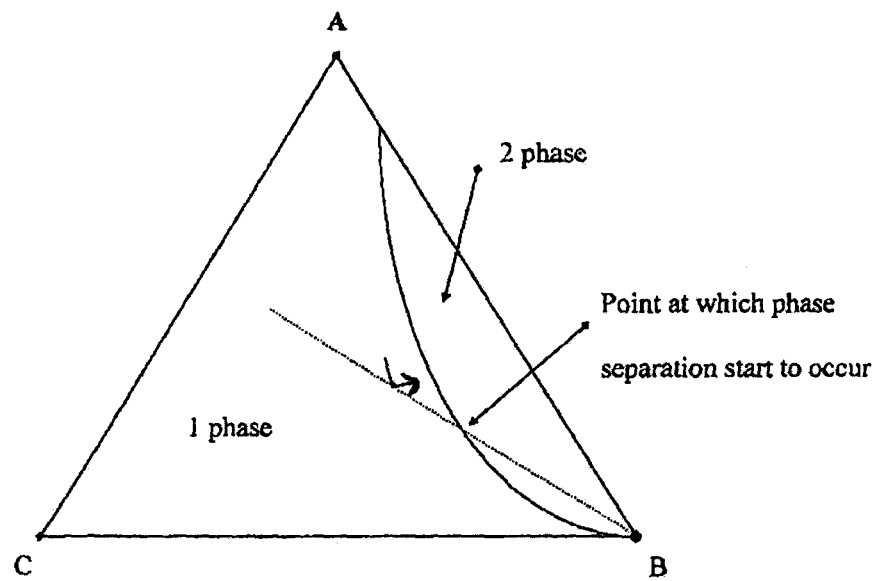
A= Active Agent; B= Polymer; C= Solvent

COATING LAYERS FOR MEDICAL DEVICES AND METHOD OF MAKING THE SAME

CROSS REFERENCE TO RELATED APPLICATION

The present application is a continuation of U.S. application Ser. No. 11/445,041, filed on May 31, 2006, published as U.S. Application Publication number 2007-0280988 A1 on Dec. 6, 2007, and issuing as U.S. Pat. No. 8,568,764, on Oct. 29, 2013, which is incorporated by reference herein as if fully set forth, including any drawings, and is incorporated by reference for all purposes.

TECHNICAL FIELD

The present invention relates generally to the field of medical devices, particularly implantable medical devices, and to methods for coating such devices with layers comprising a polymer matrix and one or more active agents. More particularly, this invention pertains to methods for controlling the morphology of coating layers and the phase distribution of components within the coating layer. This invention further pertains to methods for designing and controlling active agent release-rates from coating layers for medical devices.

BACKGROUND

In the area of medical devices, biomaterials research continues to search for new compositions and methods to improve and control the properties of the medical devices. This is particularly true for medical articles that are implantable within a subject, where predictable and controllable performance is essential to the successful treatment of a subject.

An example of an implantable medical device is a stent. Stents can act as a mechanical means to physically hold open and, if desired, expand a passageway within a subject. Typically, a stent is compressed, inserted into a small vessel through a catheter, and then expanded to a larger diameter once placed in a proper location. Stents play an important role in a variety of medical procedures such as, for example, percutaneous transluminal coronary angioplasty (PTCA), a procedure used to treat heart disease by opening a coronary artery blocked by an occlusion. Stents are generally implanted in such procedures to reduce occlusion formation, inhibit thrombosis and restenosis, and maintain patency within vascular lumens. Examples of patents disclosing stents include U.S. Pat. Nos. 4,733,665; 4,800,882; and 4,886,062.

Stents are also being developed to locally deliver active agents, e.g. drugs or other medically beneficial materials. Local delivery is often preferred over systemic delivery, particularly where high systemic doses are necessary to affect a particular site. For example, agent-coated stents have demonstrated dramatic reductions in stent restenosis rates by inhibiting tissue growth associated with restenosis.

Proposed local delivery methods from medical devices include coating the device surface with a layer comprising a polymeric matrix and attaching an active agent to the polymer backbone or dispersing, impregnating or trapping the active agent in the polymeric matrix. For example, one method of applying an active agent to a stent involves blending the agent with a polymer dissolved in a solvent, applying the composition to the surface of the stent, and removing the solvent to leave a polymer matrix in which an active agent is impregnated, dispersed or trapped. During evaporation of the solvent, phase separation can disadvantageously occur, often resulting in hard-to-control process conditions and a drug coating morphology that is difficult to predict and control. This makes delivery of the agent unpredictable.

Further, manufacturing inconsistencies among different stents can arise with the above coating method. For example, release-rate variability has been observed among supposedly identical stents made by the same process. Apparently, when some polymer coatings comprising active agents dry on the surface of a medical device different morphologies develop in different coatings, even if the coating process parameters are consistent. These differences in coating morphology may cause active agent release-rates from different stents to vary significantly. As a consequence of the inconsistent release-rate profiles among stents there can be clinical complications. Thus, there is a need for methods that can control the variability of active agent release-rates among medical devices and provide manufacturing consistency.

Morphological changes that affect release-rates of active agents have been observed to be dependent on the active agent phase in the polymer matrix. When a coating composition is applied to the surface of a medical device the active agent is initially evenly dispersed in the coating composition. However, during processing the agent may migrate or phase separate to form different phase regions within the coating layer. These regions are often connected with each other and are referred to as the percolation phase. The mass transport properties of active agents are distinct through the percolation phase. Mass transport through the percolation phase is driven by the solubility of active agent in the release medium, the diffusivity of the active agent in the release medium, and the morphological feature of the percolated phase such as, for example, tortuosity and area fraction. The release-rate of the active agent is often greatly increased from these regions or phases. The formation of percolated phases is particularly pronounced at high active agent concentrations, for example above about 35% by volume fraction of active agent to polymer in the coating layer.

Those skilled in the art will therefore appreciate that local delivery would benefit not only from improved release-rate profiles that are controlled and predictable, but also from manufacturing improvements that would provide consistency. Thus, methods for making coated medical devices with more reliable performance are highly desirable and essential to providing effective treatment of patients. In addition, control over the release-rate can assist in designing and maintaining the physical and mechanical properties of medical devices and coatings, as well.

SUMMARY

According to one aspect of the present invention, methods are provided for controlling the morphology of coating layers for medical devices comprising a polymer matrix and one or more active agents. A further aspect of the present invention provides coated medical devices with a controlled release-rate of one or more active agents by selecting the phase distribution of the active agent phases in the layer.

In some embodiments, the coating layer morphology is controlled by fixing the active agent morphology in a wet coating layer comprising one or more polymers, one or more active agents and one or more solvents. Methods to fix the active agent morphology or phase distribution include, but are not limited to, exposing to cold gas, dipping in cold liquid, exposing to shock freezing, exposing to flash vaporization, exposing to non-solvent exchange, and combinations thereof. In an alternative method, the active agent morphology is fixed by cross-linking the polymer matrix. After the active agent morphology is fixed, solvent is removed from the wet coating layer by a method such as, for example, evaporation, freeze-drying, non-solvent exchange, critical point drying, and combinations thereof. In one embodiment, solvent is removed by a combination of non-solvent exchange with $CO_2$ and critical point drying. According to a further embodiment of the present invention, a portion of the solvent is removed from the wet coating layer prior to fixing the active agent morphology. This allows modulation of the active agent phase distribution in the coating layer. Further, the embodiments of the present invention may include post-formation processing steps, such as annealing, applying a top coat and/or finishing layer, or sterilization.

According to another aspect of the present invention, selecting the phase distribution of the active agent in the polymer matrix controls the release-rate profile of active agent from a medical device coating layer. In one embodiment, the active agent phase, or phases, is fixed during coating layer formation controlling the phase distribution of the active agent. In one embodiment, the active agent phase distribution in the coating layer comprises one or more phases selected from dissolved, dispersed, and percolated phases. In one embodiment, the release-rate profile of active agent is determined by the ratio of the phases of the active agent in the coating layer.

The coating layers of the present invention may be applied to a variety of medical devices. In one embodiment, the medical device is a stent. Active agents useful in these coating layers can vary widely. In one embodiment the active agent is selected from the group consisting of antiproliferative, anti-neoplastic, anti-inflammatory, steroidal anti-inflammatory, non-steroidal anti-inflammatory, antiplatelet, anticoagulant, antifibrin, antithrombin, antimitotic, antibiotic, antiallergic, antioxidant, cytostatic agents, and combinations thereof.

BRIEF DESCRIPTION OF THE DRAWING

FIG. 1 shows a ternary phase diagram for polymer, active agent and solvent coating compositions of the present invention.

DETAILED DESCRIPTION

As discussed in further detail below, the present invention generally pertains to coating layers for medical devices, particularly implantable medical devices, comprising a polymer matrix and one or more active agents. The present invention also provides methods for forming coating layers for medical devices comprising a polymer matrix and one or more active agents, where the morphology of the coating layer and the phase distribution of the active agent within the layer are controlled by process parameters. Further, the present invention pertains to methods for controlling the morphology of coating layers, and the release-rate of active agent from the layer, by fixing the active agent phase during formation of the coating layer.

By controlling the morphology of the coating layer during formation, and particularly the active agent phase distribution within it, the release-rates of the active agent(s) from the coating layer can be more effectively controlled and manufacturing inconsistencies reduced or eliminated. Thus, improved therapeutic, prophylactic or other biological effects may be realized in the treatment of a subject. The use of process parameters in the methods of the present invention instead of additional excipients to control active agent release-rates provides advantages in the design of controlled release systems. Further, the control of active agent release-rates has positive implications for the mechanical integrity of the polymeric matrix, as well as a relationship to a subject's absorption rate of absorbable polymers.

There are many considerations in designing, controlling or predicting the active agent release-rates from a coating layer comprising a polymer matrix and one or more active agents. These include, but are not limited to, the morphology of the coating layer and components in the layer; the size and shape of the active agent; the active agent phase and the distribution of phases in the layer; the selection and the concentration of active agent or agents; the presence of polymorphism of the agents; the polymer or polymers forming the polymer matrix; the presence of functional groups on the polymers; the hydrophilicity or hydrophobicity of the polymer matrix; the presence of other additives in the composition, for example, fillers, metals, plasticizing agents, cross-linking agents; and the degree, if any, of bonding between the polymer matrix and the active agent(s).

The morphology of the coating layer is particularly important in determining the performance characteristics of coating layers, because the distribution of active agent and the phases of active agent within the polymer matrix directly relate to the active agent release-rate profile. In particular, phase separation that may occur between the solvent and the active agents and polymers of the matrix during formation of the coating layer is key to determining the coating layer morphology and the active agent release-rate profile. Thus, one of the goals of the present invention is to provide methods for controlling the morphology of coating layers comprising a polymer matrix and one or more active agents by controlling phase separations that can occur when solvent is removed from the coating composition. Yet another goal is controlling the polymer-matrix-active-agent morphology within the coating layers to provide layers with predictable active agent release-rates. The methods of the present invention use process parameters to control coating layer morphology and phase distribution of the active agent in the polymer matrix. The methods of the present invention can either decrease or increase active agent release-rates. A further aspect of the present invention provides methods for enhanced process control and coating reproducibility for medical articles and devices comprising a polymer matrix and one or more active agents.

The term "morphology" as used herein refers to the way in which a polymer matrix, optionally active agents, and optionally other components, lie in a coating layer after solvent removal. The morphology can be defined in terms of properties such as the shape, structure, form or phase of components in the coating layer. The term "configuration" is also used herein to refer to the morphology of the coating layer. In particular, morphology is used herein to describe the phase or phases of active agent and/or the arrangement of the active agent phase(s) in the polymer matrix and the distribution of those phases within the coating layer.

The morphology of the coating layer can be defined, for example, by the presence and characteristics of phase separation between components within the coating, where the phase separation can exist between polymers of the matrix, an agent and a polymer, between agents, or between other components in the polymeric matrix. In one embodiment, the coating layer morphology is defined by the phase distribution of the one or more active agent phases within the polymer matrix. In other embodiments, the morphology can be defined, for example, by the characteristics of the zone of phase separation, where the zone of phase separation can be thin, thick, continuous, non-continuous, hydrophobic, hydrophilic, porous, interconnected, dispersed, and the like. In some embodiments, the morphology can be defined, for example, by other physical characteristics of the polymeric matrix including, but not limited to, the presence of pores, crystalline or semi-crystalline regions, amorphous regions, metals, ceramics, the existence of polymorphism in agents, and the like. Any coating property that would be considered a morphological characteristic to one of skill in the art is within the scope of the present invention. The morphology can be characterized by any method or measurement known in the art to characterize layers comprising polymers.

The "phase" of a component of the coating layer can be defined, for example, by the crystallinity, semi-crystallinity, liquid crystallinity, orientation, or polymorphic state of the component. The "phase" of a component can also be defined by a distinct arrangement and/or dispersion of a component, or a fraction of a component, in the coating layer. In particular, the term "active agent phase" is used herein to refer to a physically distinct arrangement and/or distribution of some or all of the active agent species within the polymer matrix of the coating layer. The term "phase distribution" as used herein refers to the one more phases of a component present in the coating layer. In particular, phase distribution is used to refer to the distribution of one or more active agent phases in a coating layer. In one embodiment, the phase distribution of the active agent in the coating layer comprises one or more active agent phases.

The formation of an active agent phase depends on the thermodynamics and kinetics of processing. An example of a ternary phase diagram for a polymer-active-agent-solvent system is shown in FIG. 1. Kinetics of processing can be further subdivided into internal kinetic time constants and external time constants. Internal time constants include, for example, crystallization and migration rate of active agents. External time constants include, for example, the rate of solvent removal from the wet coating layer.

The methods and embodiments of the present invention are most useful where the active agent is blended with, dissolved in, impregnated, trapped or distributed in the polymer matrix. This means the active agent exists molecularly, at a molecular size, surrounded by polymer molecules of the polymer matrix. In some of these types of embodiments, the active agent is not covalently attached to the polymer matrix. The release, and hence the release-rate, of the active agent from the coating layer depends on the ability of the active agent to diffuse through the polymer matrix. This diffusion depends on the active agent phase in the layer and the transport properties of the polymeric matrix. It is one of the goals of the present invention to modulate or control the active agent phase and hence control the release-rate of the active agent from the coating layer.

In some embodiments, the active agent exists in the coating layer in a dissolved, dispersed or percolated phase. Typically, a coating layer will comprise some fraction of all three active agent phases. Without being bound by any particular theory, it is believed that the ratio of the co-existing phases is a function of the volume fraction of active agent to polymer in the coating layer, as well as the active agent's physicochemical properties, such as its solubility in the polymer matrix. Thus, at low active-agent-to-polymer ratios, for example below about 10% by volume fraction active agent to polymer, the active agent phase will predominantly be a dissolved phase. As the percentage of active agent increases, the fraction of the other phases mixed with the dissolved phase increases.

In one embodiment, the active agent of the coating layer is in a dissolved phase. In one embodiment, the active agent of the coating layer is in a dispersed phase. In one embodiment, the active agent of the coating layer is in a percolated phase. In one embodiment, the active agent of the coating layer comprises a mixed phase, wherein the phase distribution comprises two or more phases selected from the group consisting of dissolved, dispersed, or percolated phases. In one embodiment, the active agent phase distribution comprises dissolved phase, dispersed phase and percolated phase. In some embodiments, one active agent phase can primarily be present in the coating layer, whereby the particular phase is present in an amount greater than any other phase in the coating layer. In one embodiment, the active agent phase distribution comprises primarily dissolved phase. In one embodiment, the active agent phase distribution comprises primarily dispersed phase. In one embodiment, the active agent phase distribution comprises primarily dissolved and dispersed phases. The percentage of an active agent phase present in a coating layer can be controlled by the methods described herein.

As used herein, dissolved phase refers to an active agent phase in which the active agent is dissolved in the solid polymer matrix as in a solid solution. In other words, the active agent species are not closely associated with other active agent species within the coating layer and are surrounded by polymer molecules of the polymer matrix. Dissolved phases occur particularly at low active agent concentrations, where the concentration is measured as a volume fraction of the active agent to polymer in the coating layer. For example at concentrations below about 10% by volume fraction of active agent to polymer in the coating layer, and also in coating layers where no phase separation occurs between the solvent, polymer matrix and active agent. Additionally, the presence of dissolved phase depends on the active agent solubility in polymer matrix polymers. At higher volume fractions, the dissolved phase usually co-exists with other active agent phases. In one embodiment, the amount of dissolved phase in the coating layer is equal to or greater than the amount of either dispersed or percolated phase. The phase ratios depending on, for example, the active agent concentration, the degree of phase separation, and the active agent solubility in polymer matrix polymers.

At active agent concentrations of about 10% or greater by volume fraction of active agent to polymer the active agent may coalesce to form dispersed phase. As used herein, a dispersed phase refers to a phase where a number of active agent species coalesce to form active agent particles or clusters throughout the coating layer that are surrounded by polymer matrix polymer molecules. Dispersed phases can also form at lower concentrations depending on the solubility of active agent in the polymer matrix.

As used herein, percolated phase refers to an active agent phase where active agent molecules significantly migrate and/or phase separate in the polymer matrix during formation of the coating layer forming connected pathways of active agent throughout the polymer. When the active agent is present in the percolated phase, there is less control over the active agent release-rate than when the active agent is in the dissolved or dispersed phase, because the random connected pathways of active agent provide a means for the active agent to diffuse out of and be released from the coating layer. Thus, the presence of percolated active agent phase has a significant affect on the release-rate of the active agent from the coating layer. The presence of percolated phase increases the active agent release-rate. The mass transport properties of active agents are distinct through the percolation phase. The mass transport through the percolation phase is driven by the solubility of active agent in the release medium, the diffusivity of the active agent in the release medium, and the morphological feature of the percolated phase such as, for example, tortuosity and area fraction. The percolated phase is most often observed at active agent concentrations of about 35% or greater by volume fraction of active agent to polymer in the coating layer, but may also form at lower concentrations depending on the solubility of the active agent in the polymer matrix. The active agent concentration at which percolated phase becomes the predominant phase is referred to herein as the "percolation threshold." The active agent concentration at which the percolation threshold is observed depends on factors including, for example, the choice of active agent, polymer matrix and solvent, as well as those described below. In some embodiments of the present invention, the concentration of active is at the percolation threshold and the active agent is primarily in a phase other than the percolated phase.

Percolate phase formation kinetics depend on a number of factors including the active agent concentration, the solvent phase, the solvent used, the mobility of active agent, the temperature at which solvent is removed, the method of removing solvent and other processes conditions, such as the environment in which drying occurs. By using the methods described herein to fix the active agent phase in a desired phase or phase distribution before solvent removal, the degree of phase separation and dispersion of active agent within the polymer matrix can be controlled. Thus, a phase distribution profile and morphology of the coating layer can be created that provides a controllable release-rate profile for the active agent. Further, by fixing the active agent in a dissolved or dispersed phase at higher active agent concentrations more control on the release-rate is obtained because formation of percolated phase is prevented or greatly reduced. In one embodiment, percolated phase formation kinetics at high active agent concentrations are controlled by fixing the active agent phase distribution after coating a device with a coating composition. Another aspect of the present invention is to control or prevent concentration gradients of active agents from forming in the coating layer, by fixing the active agent phase distribution before removing solvent from the wet coating layer.

The coating layers of the present invention comprise a polymer matrix, including one or more polymers and one or more active agents. Optionally, the coating layer may further comprise one or more additives or other components. Typically, coating layers are formed by blending one or more active agents together with one or more polymers dissolved in a solvent to form a coating composition, applying the coating composition to a medical device surface, and removing the solvent to leave on the device active agent(s) dispersed in a polymer matrix. The morphology of the coating layer comprising a polymer matrix and one or more agents, and the phase distribution of the active agent within that layer, and hence the agent release-rate from the layer, can be profoundly affected by the manner in which the coating layer is formed and the solvent is removed from the coating composition to form a coating layer. When solvent is removed during drying, active agent dispersion and configuration within the coating layer can change due to phase separation between the solvent, and the polymer and active agent phase. This results in a coating layer morphology and distribution of active agent that is difficult to predict and control. The present invention provides methods to fix the configuration of the active agent phase and/or phase distribution prior to removing the solvent from the coating composition. In some embodiments, the methods use process parameters to control the release-rate.

One embodiment of the present invention provides methods to control the coating layer morphology by fixing the active agent morphology before or during solvent removal from the coating composition. In some of these embodiments, solvent removal forms a dried coating layer. The coating composition after being deposited on a device surface is referred to as a "wet coating layer." As used herein the term "wet coating layer" refers to a coating composition comprising solvent that has been applied to the surface of a device. A coating layer is referred to as wet until essentially all the solvent is removed from the coating layer. In the embodiments of the present invention solvent in a wet coating layer may not necessarily be in a liquid state. In one embodiment, the active agent morphology is fixed prior to solvent removal from the coating composition. Fixing the desired morphology and distribution of the active agent within the polymer matrix greatly reduces or prevents phase separation or the formation of undesired active agent phases such as, for example, dispersed or percolated phases. After the desired active agent morphology is fixed, solvent is removed to form a coating layer without affecting the fixed active agent morphology. In other embodiments, a fraction of solvent is removed before the morphology of the polymer matrix and active agent is fixed. This removal helps modulate the degree of phase separation and the distribution of active agent phases in the layer, and hence helps control the active agent release-rate. The present invention is especially useful for compositions with a high active-agent-to-polymer ratio, where phase separation or percolated phase formation are more likely. The methods of the present invention may further control or modulate the development of active agent concentration gradients within the polymer matrix.

Generally, invention coating layers provide for less variable release-rates of active agents from the coatings layers. While not being bound by any theory, apparently the fixing process renders the coating layer's thermo-mechanical and morphological properties less sensitive to subsequent processing. Apparently, controlling coating layer morphology, and hence active agent release-rates, can control or eliminate manufacturing inconsistencies.

Methods of Forming Coating Layers

The present invention provides methods for forming a coating layer for a medical device with a controlled active agent morphology. In one invention embodiment, fixing the active agent phase distribution while forming the coating layer controls the active agent release-rate.

In one embodiment of the present invention, a method for controlling coating layer morphology for a medical device comprising a polymer matrix and one or more active agents, comprises:
  (a) preparing a coating composition comprising one or more polymers, one or more active agents, and one or more solvents;
  (b) applying the coating composition onto a medical device to form a wet coating layer;
  (c) fixing the morphology of the one or more active agents; and
  (d) removing the one or more solvents from the wet coating layer to form a coating layer.

In some embodiments of the present invention, forming a medical device coating layer with a controlled active agent morphology comprises:
  (i) preparing a coating composition comprising one or more polymers, one or more active agents, and one or more solvents;
  (ii) applying the coating composition onto a medical device to form a wet coating layer;
  (iii) removing a fraction of the one or more solvents from the wet coating layer;
  (iv) fixing the active agent morphology; and
  (v) removing the remaining solvent(s) to form a coating layer.

As used herein the terms "fix," "fixed," "fixes" or "fixing" are used interchangeably to refer to where a component of the coating layer is restricted or prevented from changing its morphology or phase distribution so that the morphology or phase distribution becomes insensitive to subsequent process steps. This definition applies principally to the active agent component and not to the polymer matrix of the coating layer. Although the morphology of the polymer matrix can also be fixed, it is more likely to change during post-processing steps, for example annealing. When fixed the morphology, configuration or phase of a component substantially remains in that phase, and does not significantly change to other phases when the coating layer is subjected to further process steps. For example, fixing an active agent in the dissolved phase prevents, restricts, or greatly reduces movement or diffusion of the active agent to form other phases, thus preserving an earlier-in-time active agent phase distribution. When fixed, the molecular arrangement in the coating layer will usually not be in thermodynamic equilibrium.

Embodiments of the present invention may further comprise after step (d), or step (v) one or more optional post-formation process steps. For example, post-formation process steps include, but are not limited to, annealing the coating layer, applying a topcoat or barrier layer to the surface of the polymer-matrix-active-agent coating layer, applying an optional finishing coat layer, and sterilization. Other post-process steps or combinations of post-process steps may also be used in the practice of the invention. In one embodiment, the methods comprise subjecting the coating layer formed in step (d) or (v) to one or more post-formation process steps.

Various methods can be employed in embodiments of the present invention to fix the morphology or configuration of the one or more active agents of the coating layer. Suitable methods to fix the active agent morphology include, but are not limited to, rapidly cooling the wet coating layer by exposing it to a cold gas; freezing the wet coating layer by dipping it into a cold liquid, for example, liquid nitrogen; exposing to shock freezing by applying the coating composition to a cooled device surface; exposing to flash vaporization by applying the coating composition to a hot device surface; and exposing to non-solvent exchange by exchanging the solvent for a non-solvent for the active agent. Other methods to fix the active agent configuration include, but are not limited to, cross-linking the polymer matrix.

In one embodiment of the present invention, rapid cooling is used to fix the active agent morphology. In some embodiments, the coating composition is applied onto the medical device and then rapidly cooled, for example by exposing the wet coating layer to cold liquid, cold gas, or other low temperature environment. For example, the coating composition can be applied to a stent, and the stent then can be dipped in liquid nitrogen or exposed to cold gas to fix the configuration. Other cold liquids may also be used to rapidly cool the coating layer. Typically, the coating composition is cooled to a temperature of 10° C. or less, alternatively 0° C. or less, −10° C. or less, −20° C. or less, −50° C. or less, −100° C. or less, −150° C. or less, and −180° C. or less. Any solvent remaining in the coating layer after the desired configuration is fixed can subsequently be removed, for example, by sublimation (freeze-drying) or other suitable method.

Without being bound by any particular theory, fixing the active agent morphology in the coating layer prior to removing the solvent and drying the layer apparently locks the active agent into a desired configuration rendering the thermo-mechanical and morphological properties of the active agent and coating layer insensitive to subsequent process parameters, such as, for example, removing solvent, drying the coating, annealing and sterilizing, as well as improving the device shelf-life. This significantly avoids or prevents forming dispersed or percolated phases due to phase separation and helps control the active agent release-rate.

In another embodiment of the present invention, the active agent configuration is fixed by exposing to shock freezing at the time the coating composition is deposited onto the medical device surface. Depositing the coating composition onto a surface of a cooled medical device can accomplish this. Typically, the device is cooled to a temperature of 10° C. or less, alternatively 0° C. or less, −10° C. or less, −20° C. or less, −40° C. or less, −70° C. or less, −100° C. or less, −150° C. or less, and −200° C. or less. Subsequently, sublimation (freeze drying) or other suitable method removes any remaining solvent.

In one embodiment of the present invention, flash vaporization of the solvent while depositing the coating composition fixes the active agent configuration. Without being bound by any theory, rapidly vaporizing or atomizing the solvent phase during deposition of the coating composition apparently locks the active agent morphology, and controls the release-rate profile of the active agent by, for example, preventing dispersed or percolated phase formation. For example, spraying the coating onto a hot medical device may cause this to occur. In one embodiment of the present invention, depositing the coating composition onto a hot medical device is used to fix the polymer-matrix-active-agent configuration. Applying the coating composition onto a hot surface immediately atomizes or flash vaporizes the volatile solvent, thereby fixing or locking the active agent into the desired configuration. When flash vaporization is chosen to fix the active agent configuration, the solvent should be selected to readily evaporate or atomize. Typically, the surface is heated to a temperature of 30° C. or more, alternatively 45° C. or more, 60° C. or more, 75° C. or more, 100° C. or more, 150° C. or more, 200° C. or more, 300° C. or more, and 400° C. or more. Depositing the coating composition onto a hot surface may also fix the active agent morphology by initiating polymer matrix cross-linking for those compositions comprising cross-linking agents, groups, or initiators. Residual solvent remaining in the coating layer may be removed by one of the methods described herein.

In yet other embodiments, the coating layer configuration is fixed after applying the coating composition to a device in a solvent-saturated atmosphere. Depositing the coating layer in a saturated solvent atmosphere minimizes solvent loss due to evaporation from the applied coating composition. These conditions minimize morphology changes, such as active agent precipitation in the coating layer due to solvent loss, preserving the as-coated polymer matrix and active agent morphologies. In some embodiments, this is done to minimize solvent losses when applying the coating composition by spray atomization, where between 80-90% of the solvent is normally lost.

In yet another embodiment of the present invention, exposing the coating layer to a non-solvent for the active agent controls the polymer-matrix-active-agent configuration. For example, this may be accomplished by exposing the polymer-matrix-active-agent coating layer to a non-solvent for the active agent, whereby the non-solvent is exchanged for the solvent. By controlling the non-solvent exchange kinetics a coating layer morphology can to be selected with a desired active agent phase distribution. In some embodiments, the non-solvent for the active agent should be miscible with the coating composition solvent. Examples of suitable non-solvents for the active agents include, but are not limited to, supercritical $CO_2$, isopropyl alcohol, acetone, heptane and hexane, and blends thereof. Other examples of suitable solvents include, but are not limited to, fluorocarbons and chlorofluorocarbons such as, for example, Freon™ and HCFC 141b (dichlorofluoroethane), and blends of fluorocarbons and alcohol such as, for example, dichlorofluoroethane blended with ethanol. Non-solvent exchange may be carried out by method such as, for example, liquid, spray or vapor mist contact. The active agent non-solvent is subsequently removed to form a coating layer by one of the methods described herein. If supercritical $CO_2$ is used as the non-solvent for the active agent critical point drying can be used to form the coating layer.

In some embodiments of the present invention, non-solvent exchange combined with one of the other methods described herein is used to fix the coating layer morphology and active agent configuration. For example, after non-solvent exchange the configuration of the polymer matrix-active agent may be fixed by exposing the coating layer to liquid nitrogen. A desired phase separation of the active agents into the remaining coating layer solvent can be induced by partial non-solvent exchange, for example with supercritical $CO_2$, after which exposing the coating layer to liquid nitrogen or other morphology fixing method described herein can fix the selected configuration. Any remaining solvent can be removed by one of the methods described herein. For example, this method can increase the release-rate of a portion of the active agent by forming a desired amount of percolated phase within the coating layer.

In yet another embodiment of the present invention, cross-linking the polymer or polymers of the polymer matrix after coating the medical device with the coating composition can fix the coating configuration, thereby locking the active agent into the desired phase structure, distribution, or morphology. Cross-linking can be accomplished by the choice of polymers or prepolymers used to form the polymer matrix and, if necessary, the addition of a free radical or other cross-linking initiator or agent to the coating composition. The cross-linking agent or initiator can be added, for example in step (a) or (i) above, to the coating composition, applied to the surface of the medical device and the polymer matrix cross-linking activated before solvent removal. Solvent remaining in the coating layer after cross-linking may subsequently be removed, for example, by evaporation, sublimation or other suitable method without inducing phase separation in the active agent. After cross-linking the coating composition the coating layer may be subjected to additional steps, for example, dipping in liquid nitrogen before removing the solvent by freeze-drying.

Examples of suitable methods for initiating cross-linking include, but are not limited to, heat (thermal initiators), light, ultraviolet (UV) radiation, infrared (IR) radiation, electron beam radiation or gamma radiation. In some embodiments, initiating cross-linking by a method that does not heat the coating composition aids in protecting heat sensitive active agents.

Cross-linking agents and initiators include, but are not limited to, photosensitizers for radiation curing of any monomers and macromonomers; catalysts for non-radiation curing of any monomers, macromonomers, or polymers; and cross-linking agents such as zirconium compounds, aziridines, and isocyanates. Useful linking agents include, but are not limited to, agents bearing hydroxyl, epoxide, carboxyl, amino, imide, aziridine, thiol, phosphoryl, aldehyde, anhydride, acyl halide, silyl, isocyanate, diisocyanate, carbodiimide, dihydrazide, multiaziridine, multifunctional carbodiimide, isothiocyanate or diamine functionalities. Further useful linking agents include, but are not limited to, polymers bearing a primary amine side group or groups, N-hydroxy-succinimide, acryloxy-terminated polyethylene glycol, and methacryloxy-terminated polyethylene glycol. Examples of cross-linking agents and initiators include, but are not limited to, formaldehyde, dialdehydes such as glutaraldeyde or succindialdehyde, di-epoxy reagents, diacrylates and methacrylates such as polyethyleneglycol diacrylate, dia-azo compounds, di-N-hydroxy succinimide compounds, succinic anhydride, maleic anhydride, acetophenone, 2,2-dimethoxy-2-phenylacetophenone, 1-hydroxycyclohexyl phenyl ketone, benzoin ethyl ether, benzophenone, camproquinone, and ethyl-4-N,N-dimethyl aminobenzoate. Examples of thermal initiators include, but are not limited to, those which form free radicals at moderate temperatures, such as benzoyl peroxide with or without triethanolamine, potassium persulfate with or without tetremethylethylenediamine, perammonium sulfate with sodium bisulfite, bis(2,4-dichlorobenzoyl)peroxide, dicumyl peroxide, 2,5-bis(tertbutyl peroxy)-2,5-dimethyl hexane and 2,2'-azobisisobutyronitrile.

Another aspect of the present invention is to control the fraction of solvent removed from the wet coating layer before the desired active agent morphology is fixed. By removing a known solvent fraction after applying the coating composition, the morphology of the polymer-matrix-active-agent coating layer can be designed to have a selected amount of phase separation between the solvent and the polymer matrix and active agent phase, and thus a predetermined fraction of an active agent phase. Hence, the active agent release-rate can be modified for the most beneficial therapeutic effect in a subject.

In some embodiments, between about 1 and 90%, alternatively, between about 1 and 80%, about 1 and 70%, about 1 and 60%, about 1 and 50%, about 1 and 25%, or about 1 and 10%, by weight of the solvent in the coating composition is removed from the coating layer before the polymer-matrix-active-agent configuration in the coating layer is fixed.

The percentage of an active agent phase present in a coating layer can be selected by the methods described herein. The amount of a particular active agent phase present in the coating layer can vary considerably over the range from 0% to 100% based in the total amount of active agent in the coating layer. In one embodiment, the percentage of dissolved phase is greater than the combined amount of dispersed and percolated phase. In other embodiments, the percentage of dissolved phase is equal to or greater than the percentage of either dispersed or percolated phase in the coating layer. In yet other embodiments, the percentage of dissolved phase is less than the percentage of dispersed or percolated phase in the coating layer. Designing the percentage of active agent in different phases can select the most therapeutically effective release-rate. In some embodiment, the release-rate profile of active agent from the coating layer is determined by the ratio of the phases of the active agent in the coating layer.

Coating layer thickness is from about 0.1 nm to about 1.0 cm, from about 0.1 nm to about 1.0 mm, from about 0.1 nm to about 100 μm, from about 0.1 nm to about 1 μm, from about 0.1 nm to about 100 nm, from about 0.1 nm to about 10 nm, from about 10 nm to about 100 nm, from about 0.5 μm to about 10 μm, from about 1 μm to about 10 μm, from about 10 μm to about 50 μm, from about 50 μm to about 100 μm, or any range therein. In other embodiments, the thickness of the coating layer can be regionally distributed throughout a device to create a variation in thicknesses such as, for example, the variation in thicknesses present in an abluminally-coated drug-eluting stent (DES) systems.

Coating Compositions

The coating compositions of the present invention comprise one or more active agents, one or more polymers, and one or more solvents. Optionally, the coating composition may further comprise one or more additives or other components such as, for example, plasticizing agents, metals, metal oxides or ceramics.

Coating compositions are prepared by conventional methods, wherein all components are combined and then blended. More particularly, adding a predetermined amount of polymer to a predetermined amount of a compatible solvent forms a polymer solution. The polymer can be added to the solvent at ambient pressure, and under anhydrous or other atmosphere. If necessary, gentle heating and stirring or mixing can cause the polymer to dissolve into the solvent, for example, 12 hours in a 60° C. water bath.

Sufficient amounts of active agent are dispersed in the blended polymer solution. The active agent preferably should be in true solution or saturated in the blended composition. If the active agent is not completely soluble in the composition, operations including mixing, stirring, or agitation can be employed to homogenize the residuals. Alternatively, active agent can first be added to a compatible solvent before mixing with the polymer solution. Optionally, a second solvent, such as tetrahydrofuran or dimethylformamide, can be used to improve the solubility of an active agent in the coating composition or to increase the composition's wetting ability. The second solvent can be added to the coating composition or the active agent can be added to the second solvent before mixing with the polymer solution.

If additives and other components, for example cross-linking agents, plasticizers, or ceramics, are used these may be added and blended with the coating composition at any step.

The amount of active agent in the coating layer should be the dosage or concentration required to produce a therapeutic effect, and greater than the level at which non-therapeutic results are obtained. The dosage or concentration of the active agent depends upon factors such as, for example, the particular circumstances of the subject, the nature of the trauma, the nature of the therapy desired, the time over which the ingredient administered resides at the vascular site; and if other bio-active substances are employed, the nature and type of the substance or the combination of substances. The therapeutically effective dosage can be determined by methods known in the art, such as for example, conducting suitable in vitro studies.

The one or more polymers of the polymer matrix can comprise from about 0.1% to about 35%, and more narrowly from about 2% to about 20% by weight of the total weight of the coating composition. The one or more solvents may comprise from about 19.8% to about 99.8%, more narrowly from about 49% to about 87%, and yet more narrowly from about 79% to about 87% by weight of the total weight of the coating compositions. The one or more active agents may comprise from about 0.02% to about 40%, preferably from about 0.1% to about 9%, and more narrowly from about 0.7% to about 1.2% by weight of the total weight of the coating composition. Selection of a specific weight ratio of the polymer and solvent depends on factors such as, but not limited to, the material from which the device is made, the geometrical structure of the device, and the type and amount of active agent employed. The specific weight percent of active agent depends on the polymer matrix-active agent morphology of the coating layer and phases of active agent required, and factors such as the dosage, duration of the release, cumulative amount of release, and the release-rate desired.

Solvents

The solvent should be capable of dissolving the polymer at the concentration desired in the coating solution. Solvents useful for forming the coating compositions of the present invention are chosen based on factors such as, for example, the solubility of the one or more polymers in the solvent, compatibility with the active agents, the volatility of the solvent, and the ability of the solvent to be removed from the coating layer after the coating layer configuration is fixed. Any suitable solvent, or mixture of solvents, that meets the criteria for a coating solvent can be used.

Examples of suitable solvents for the practice of the present invention include, but are not limited to, dimethylacetamide, dimethylformamide, tetrahydrofuran, cyclohexanone, acetone, acetonitrile, i-propanol, n-propanol, methanol, ethanol, butanol, propylene glycol monomethyl ether, methyl butyl ketone, methyl ethyl ketone, diethyl ketone, ethyl acetate, n-butyl acetate, dioxane, chloroform, water (buffered saline), dimethylsulfoxide, dimethylformide, benzene, toluene, xylene, hexane, cyclohexane, pentane, heptane, octane, nonane, decane, decalin, i-butyl acetate, i-propyl acetate, diacetone alcohol, benzyl alcohol, 1-butanone, 2-butanone, N-methylpyrrolidinone, methylene chloride, carbon tetrachloride, tetrachloroethylene, tetachloroethane, chlorobenzene, 1,1,1-trichloroethane, formamide, hexafluoroisopropanol, 1,1,1-trifluoroethanol, hexamethyl phosphoramide, and combination thereof.

Application of Coating Composition onto a Medical Device.

Application of the coating composition onto the medical device can be accomplished by any method known in the art. For example, the coating composition may be applied to the medical device by casting, spraying, dipping or immersing, direct dispensing by hand or injection. The coating compositions of the present invention may be applied to all or to selected surfaces of a device. In alternative embodiments, where the coating composition is used to form a medical device, the coating composition can be injection molded or formed by other method known in the art.

Operations such as wiping, centrifugation, blowing or other web-clearing acts may be performed to achieve a more uniform coating. Briefly, wiping refers to physical removal of excess coating from the surface of the device; centrifugation refers to the rapid rotation of the device about an axis of rotation; and blowing refers to application of air at a selected pressure to the deposited coating. Excess coating may also be vacuumed off the surface of the device.

Before applying the coating layer to a medical device, the surface of the device should be clean and free from contaminants that may be have been introduced during manufacture. However, no particular surface treatment is required prior to applying the coating composition. Metallic surfaces of stents can, for example, be cleaned by an argon plasma process as is known to one of ordinary skill in the art.

A primer layer may optionally be used in the embodiments of the present invention to aid the adhesion of the coating layer to the device surface. This is particularly useful when the presence or concentration of the active agent in the polymer matrix interferes with the ability of the polymer matrix to adhere effectively to the device surface. If an optional primer layer is used, the primer layer is coated on the device or a portion of the device by any method described herein or known to one of ordinary skill in the art. The primer layer is dried (solvent removed) or cured before the coating composition comprising the polymer matrix and active agent is applied to the surface of the primer layer. Primer compositions may be prepared by adding a predetermined amount of one or more polymers to a predetermined amount of solvent or mixture of solvents. Representative examples of polymers for the primer layer include, but are not limited to, polyisocyanates, polyethers, polyurethanes, acrylates, titanates, zirconates, silane coupling agents, high amine content polymers, polymers with a high content of hydrogen bonding groups, and unsaturated polymers and prepolymers. Representative examples of polymers also include those polymers used in the polymer matrices of the present invention as described herein. Further examples of primer layers useful for the medical devices of the present invention include those disclosed in U.S. Pat. No. 6,908,624 to Hossainy et al., the disclosure of which is incorporated herein by reference.

Drying Coating Compositions

After coating the medical device and fixing the active agent morphology, solvent remaining in the wet coating layer is removed to form a dry coating layer. It is understood that by drying substantially all the solvent, and wetting fluid if used, will be removed from the coating layer, but traces or residues can remain blended with the polymer. In order not to change the fixed morphology of the active agent in the coating layer, the selected method should remove the solvent without causing undesired phase separations or phase changes. Suitable methods for removing the solvent from the coating composition include, but are not limited to, evaporation, freeze-drying (sublimation), non-solvent exchange, critical point drying, or any combination thereof. Removal of the solvent may occur in a controlled atmosphere, for example humid, anhydrous or solvent saturated, at ambient pressure or under vacuum. The temperature at which the solvent is removed will depend on the method, and may vary over a wide range.

In one embodiment of the present invention, solvent in the wet coating layer is removed by freeze-drying. The method comprises first freezing the coating layer, if the layer is not already in a frozen state, and then placing the medical device under reduced pressure or in a vacuum so that the solvent molecules vaporize (sublime) without the solvent passing through a liquid phase. The rate at which the coating layer is frozen and solvent removed may vary over a wide range. In one embodiment, the coating layer is frozen to 0° C. or less, alternatively to −40° C. or less, −70° C. or less, −100° C. or less, and −150° C. or less.

In embodiments where the active agent morphology is fixed by shock freezing or another method of reducing the temperature of the coating layer, solvent remaining in the coating layer can be removed, for example, by freeze-drying the coating layer.

Evaporation of the solvent can occur at room temperature or be induced by heating the device to a temperature for a period of time. Removal of the solvent may also occur in a controlled atmosphere, for example humid, anhydrous or solvent saturated, at ambient pressure or under vacuum. Conditions should be chosen so that they do not substantially adversely affect the active agent or the configuration of the active agent. The coating layer can be heated at a temperature for a period of time, for example, at 60° C. for 10 to 24 hours. The heating temperature is chosen so as not to exceed temperatures at which the active agent is adversely affected.

In embodiments of the present invention where cross-linking is used to fix the active agent phase in the polymer matrix, a method such as, for example, evaporation can remove residual solvent as described above. Solvent may also be removed by freeze-drying the coating layer after cross-linking by freezing the coating layer and then freeze-drying. Other methods, as described herein, may also be used to remove any remaining solvent from coating configurations fixed by cross-linking.

In yet another embodiment of the present invention, solvent of the coating layer can be removed from the coating layer by exchange with a non-solvent for the active agent, and subsequent removal of the non-solvent by one of the methods described herein. This can be accomplished, for example, by exposing the wet polymer-matrix-active-agent coating layer to the non-solvent. The chosen non-solvent should be miscible with the solvent of the coating composition. In some invention embodiments, the non-solvent is substantially miscible with the coating composition solvent. Examples of suitable non-solvents for the active agents include, but are not limited to, supercritical $CO_2$, isopropyl alcohol, acetone, heptane and hexane, and blends thereof. Other examples of suitable solvents include, but are not limited to, fluorocarbons and chlorofluorocarbons, for example Freon™ and HCFC 141b (dichlorofluoroethane), and blends of fluorocarbons and alcohol such as, for example, dichlorofluoroethane blended with ethanol. Non-solvent exchange may be carried out, for example, by method such as liquid, spray or vapor mist contact. In those embodiments where supercritical $CO_2$ is used as the non-solvent for the active agent, the coating layer may be dried by critical point drying. In some embodiments the coating layers of the present invention is dried by critical point drying.

Post-Formation Processing Steps

After drying the coating layers by removing solvent from the wet coating, post-formation treatments optionally may be performed to the coating layers and medical devices. Optional post-processing steps include, but are not limited to, annealing the coating layer, applying a protective coating, applying a rate-reducing membrane, diffusion barrier layer or topcoat layer to the coating layer surface, applying an optional finishing coat layer, and sterilization. The medical devices may further comprise an optional top-coat or barrier layer that, in some embodiments, controls the diffusion of the active agent out of the coating layer. Outer coating layers can be applied over all or only a portion of the coating layer comprising the active agent. Examples of topcoat layers and finishing coat layers are described, for example, in U.S. Patent Application Publication No. US 2005/0191332 to Hossainy, the disclosure of which is incorporated herein by reference. Further examples of outer layers, including rate-reducing membranes and diffusion barrier layers, are described in U.S. Pat. No. 6,908,624 to Hossainy et al., the disclosure of which is incorporated herein by reference. In some embodiments, the coating layer is annealed to remove stresses. In these or other embodiments, annealing ameliorates coating layer brittleness caused by, for example, freeze-drying.

Medical Devices

Throughout this application "medical device" or "medical article" are used interchangeably, and refer to any device or article that can be used in the medical treatment of a human or veterinary subject. Medical devices may be used either externally on a subject or implanted in a subject. In a preferred embodiment, the medical device is implantable. An example of an implantable medical device is a stent, which can be implanted into a human or veterinary patient. While examples of coating a device such as a drug eluting or delivery stent are described herein, one of skill in the art will appreciate that other medical devices and substrates can be manufactured using the methods of the present invention. Examples of medical devices include, but are not limited to, stents, stent-grafts, vascular grafts, artificial heart valves, foramen ovale closure devices, cerebrospinal fluid shunts, pacemaker electrodes, guidewires, ventricular assist devices, cardiopulmonary bypass circuits, blood oxygenators, coronary shunts vena cava filters, and endocardial leads. Examples of stents include, but are not limited to, tubular stents, self-expanding stents, coil stents, ring stents, multi-design stents, and the like. In some embodiments, the stents include, but are not limited to, vascular stents, renal stents, biliary stents, pulmonary stents and gastrointestinal stents.

The underlying structure of the medical device can be virtually any design. The medical device can be comprised of a metallic material or alloy, low-ferromagnetic, non-ferromagnetic, biostable polymeric, biodegradable polymeric, bioabsorbable polymers, biodegradable metallic or other compatible material known in the art. In yet further embodiments, the medical devices may be formed from the coating compositions comprising one or more polymers and one or more active agents by, for example, injection molding and other methods as known to one skilled in the art. Examples of metals and alloys include, but are not limited to, ELASTINITE®, NITINOL® (Nitinol Devices and Components, Fremont, Calif.), stainless steel, tantalum, tantalum-based alloys, nickel-titanium alloys, platinum, platinum-based alloys such as, for example, platinum-iridium alloys, iridium, gold, magnesium, titanium, titanium-based alloys, zirconium-based alloys, alloys comprising cobalt and chromium (ELGILOY®, Elgiloy Specialty Metals, Inc., Elgin, Ill.; MP35N and MP20N, SPS Technologies, Jenkintown, Pa.) or combinations thereof. The trade names "MP35N" and "MP20N" describe alloys of cobalt, nickel, chromium and molybdenum. The MP35N consists of 35% cobalt, 35% nickel, 20% chromium, and 10% molybdenum. The MP20N consists of 50% cobalt, 20% nickel, 20% chromium, and 10% molybdenum.

Active Agents

The coating compositions of the present invention comprise one or more active agents. If combinations of active agents are used, each agent is chosen with regard to its compatibility with other agents and polymers of the matrix, and with regard to its release-rate from the polymer matrix. The term "active agent" refers to any substance that is capable of providing a therapeutic, prophylactic or other biological effect within a subject. An active agent can also be a diagnostic agent, or be for enhancing wound healing in a vascular site or improving the structure and elastic properties of a vascular site. An active agent can be a drug. Examples of suitable active agents include synthetic inorganic and organic compounds, proteins and peptides, polysaccharides and other sugars, lipids, and DNA and RNA nucleic acid sequences having therapeutic, prophylactic or diagnostic activities.

Active agents of the coating compositions can form linkages with the polymer matrix when blended or mixed into the coating composition or formed into coatings of the present invention. If linkages form the connections may be physical, chemical, or a combination thereof. Examples of physical connections include, but are not limited to, an interlinking of components that can occur, for example, in interpenetrating networks and chain entanglement. Examples of chemical connections include, but are not limited to, covalent and non-covalent bonds. Non-covalent bonds include, but are not limited to, ionic bonds and inter-molecular attractions such as, for example, hydrogen bonds and electrostatic interactions or attractions. The polymers can also be blended or mixed with the active agents. In some embodiments, the active agents do not form covalent bonds with the polymer matrix. If more than one agent is present in the coating, each agent may form a different type of linkage or no linkage.

A wide range of different active agents can be incorporated into the medical devices of the present invention. These include hydrophobic, hydrophilic, and high molecular weight macromolecules such as proteins. The active agent can be incorporated into a polymeric matrix in a percent loading of between 0.01% and 70%, alternatively, between 5% and 50% by weight.

Examples of active agents include, but are not limited to, antiproliferative, antineoplastic, anti-inflammatory, steroidal anti-inflammatory, non-steroidal anti-inflammatory, antiplatelet, anticoagulant, antifibrin, antithrombin, antimitotic, antibiotic, antiallergic, antioxidant, and cytostatic agents, and combinations thereof.

Examples of antiproliferative substances include, but are not limited, to actinomycin D, or derivatives and analogs thereof (manufactured by Sigma-Aldrich of Milwaukee, Wis., or COSMEGEN available from Merck, Whitehouse Station, N.J.). Synonyms of actinomycin D include dactinomycin, actinomycin IV, actinomycin $I_1$, actinomycin $X_1$, and actinomycin $C_1$. Examples of antineoplastics and/or antimitotics include, but are not limited to, paclitaxel (e.g. TAXOL® by Bristol-Myers Squibb Co., Stamford, Conn.), docetaxel (e.g. TAXOTERE®, from Aventis S.A., Frankfurt, Germany), methotrexate, azathioprine, vincristine, vinblastine, fluorouracil, doxorubicin hydrochloride (e.g. ADRIAMYCIN® from Pharmacia & Upjohn, Peapack, N.J.), and mitomycin (e.g. MUTAMYCIN® from Bristol-Myers Squibb Co., Stamford, Conn.). Examples of antiplatelets, anticoagulants, antifibrins, and antithrombins include, but are not limited to, heparin, sodium heparin, low molecular weight heparins, heparin sulfate, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as ANGIOMAX™ (bivalirudin, Biogen, Inc., Cambridge, Mass.), and 7E-3B® (an antiplatelet drug from Centocor, Horsham, Pa.). Examples of suitable antimitotic agents include, but are not limited to, methotrexate, azathioprine, vincristine, vinblastine, fluorouracil, adriamycin, and mutamycin. Examples of such cytostatic or antiproliferative agents include, but are not limited to, angiopeptin, angiotensin converting enzyme inhibitors such as captopril (e.g. CAPOTEN® and CAPOZIDE® from Bristol-Myers Squibb Co., Stamford, Conn.), cilazapril or lisinopril (e.g. PRINIVIL® and PRINZIDE® from Merck & Co., Inc., Whitehouse Station, N.J.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name MEVACOR® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include, but are not limited to, alpha-interferon, genetically engineered epithelial cells, tacrolimus, dexamethasone, and rapamycin and structural derivatives or functional analogs thereof, such as 40-O-(2-hydroxyl)ethyl-rapamycin (known by the trade name of Everolimus available from Novartis Pharma AG, Switzerland), 40-O-(3-hydroxyl) propyl-rapamycin, 40-O-[2-(2-hydroxyl)ethoxy]ethyl-rapamycin, and 40-O-tetrazole-rapamycin.

Example of diagnostic agents include, but are not limited to, those detectable by x-ray, fluorescence, magnetic resonance imaging, radioactivity, ultrasound, computer tomography (CT), and positron emission tomography (PET).

The foregoing substances are listed by way of example and are not meant to be limiting. Other active agents that are currently available or that may be developed in the future are equally applicable.

Polymer Matrices

The coating layers of the present invention comprise a polymer matrix, composed of one or more polymers. The one or more polymers comprising the polymer matrix may be in mixed, blended or conjugated form. The polymer matrices and coating compositions of the present invention may also be used to form medical devices by a process such as, for example, molding.

There is a wide choice of polymer and copolymers for use in the polymer matrix of the present invention. The chosen polymer matrix must be one that is biocompatible and minimizes irritation when implanted. The choice of the matrix components depends on numerous factors including, but not limited to, the interactions between the polymer(s) and the agent(s) and/or solvent(s), the biocompatibility of the polymer(s), and the physical, mechanical, chemical and biological properties of the polymers. Performance parameters include, for example, the ability to adhere to the surface of the medical device, the toughness of the coating desired, the capacity for the loading concentration of an agent, and the rate of biodegradation and elimination of the composition from a subject.

Each of the one or more polymers chosen for the matrix can be either biostable or biodegradable. "Biodegradable" refers to polymers that are capable of being completely degraded and/or eroded when exposed to bodily fluids such as blood and can be gradually resorbed, absorbed and/or eliminated from the subject. The process of breaking down and eventual absorption and elimination of the polymer can be caused by, for example, hydrolysis, metabolic processes, bulk or surface erosion, and the like. After biodegradation traces or residual polymer may remain on the device or near the device. Examples of biodegradable polymers include, but are not limited to, polymers having repeating units such as, for example, an α-hydroxycarboxylic acid, a cyclic diester of an α-hydroxycarboxylic acid, a dioxanone, a lactone, a cyclic carbonate, a cyclic oxalate, an epoxide, a glycol, an anhydride, a lactic acid, a glycolic acid, a lactide, a glycolide, an ethylene oxide, an ethylene glycol, or combinations thereof. In some embodiments, the polymer matrix releases active agent during biodegradation. In other embodiments, the polymer matrix releases active agent without biodegradation of the matrix. In yet other embodiments, the release of active agent may be partially dependent on biodegradation of the polymer matrix. Biostable polymers should have a relatively low chronic tissue response.

The polymers useful for the polymer matrixes of the present invention include, but are not limited to, natural or synthetic polymers, condensation polymers, homopolymers and copolymers or any combination and/or blend thereof. Polymers may be hydrophobic, hydrophilic, or a combination thereof. Copolymers may be random, alternating, block, graft, and/or crosslinked, and may include polymers with more than two different types of repeating units such as terpolymers. In some embodiments, the polymers are selected such that they specifically exclude any one or any combination of any of the polymers taught herein.

Representative examples of polymers that can be used in the polymer matrices and coating compositions of the present invention include, but are not limited to, poly(acrylates) (such as poly(methacrylates), polymethyl methacrylate and polybutyl methacrylate), acrylic polymers and copolymer (such as polyacrylonitrile), poly(cyanoacrylates), fluorinated polymers or copolymers (such as polyfluoro-alkylenes, polyvinylidene fluoride-co-hexafluoropropene and polytetrafluoroethylene), polycaprolactones, polylactides, poly(D-lactides), poly(L-lactides), poly(D,L-lactides), Poly(lactic acids), poly (glycolic acid), poly(lactide-co-glycolide), poly(glycolic acid-co-trimethylene carbonate), poly(lactic acid-co-trimethylene carbonate, poly(amino acids), polyhydroxyalkanoates, poly(hydroxyvalerate), polyhydroxybutyrates, poly(hydroxybutyrate-co-valerate), polymers and copolymers of hydroxylethyl methacryate, polydioxanones, polyorthoesters, polyanhydrides, polyphosphoesters, polyphosphoester urethanes, polyphosphazenes, polycarbonates, polyiminocarbonates, polytrimethylene carbonates, co-poly (ether-esters) (such as polyethylene oxide/polylactic acid (PEO/PLA)), poly(alkylene oxalates), polyurethanes, silicones, polyesters, polyolefins (such as polyethylene and polypropylene), poly(isobutylene) and ethylene-alphaolefin copolymers, vinyl halide polymers and copolymers (such as polyvinyl chloride), polyvinyl ethers (such as polyvinyl methyl ether), polyvinylidene halides (such as polyvinylidene fluoride and polyvinylidene chloride), polyacrylonitrile, polyvinyl ketones, polyvinyl aromatics (such as polystyrene), polyvinyl esters (such as polyvinyl acetate), copolymers of vinyl monomers with each other and olefins (such as ethylene-methyl methacrylate copolymers, acrylonitrile-styrene copolymers, ABS resins, and ethylene-vinyl acetate copolymers), ethylene vinyl alcohol copolymers (such as ethylene vinyl alcohol co-polymer, commonly know by the generic name EVOH or by the trade name EVAL), polyamides (such as Nylon 66 and polycaprolactam), alkyd resins, polyoxymethylenes, polyimides, polyester amides, polyethers including poly(alkylene glycols) (such as poly (ethylene glycol) and poly(propylene glycol)), poly(tyrosine derived carbonates), poly(tyrosine derived arylates), epoxy resins, rayon, rayon-triacetate, biomolecules (such as fibrin, fibrinogen, starch, cellulose, collagen, hyaluronic acid), poly (N-acetylglucosamine) (chitin), chitosan, cellulose, cellulose acetate, cellulose butyrate, cellulose acetate butyrate, CELLOPHANE, cellulose nitrate, cellulose propionate, cellulose ethers, and carboxymethyl-cellulose, and derivatives, copolymers and combinations of the foregoing. In some embodiments, the polymer can exclude any one or any combination of the aforementioned polymers.

Plasticizing Agents

The coating compositions and coating layers of the present invention may further comprise one or more plasticizing agents. The terms "plasticizer" and "plasticizing agent" can be used interchangeably in the present invention, and refer to any agent, including any agent described above, where the agent can be added to a polymeric composition to modify the mechanical properties of the composition or a product formed from the composition. Plasticizers can be added, for example, to reduce crystallinity, lower the glass-transition temperature $(T_g)$, or reduce the intermolecular forces between polymers. The mechanical properties that are modified include, but are not limited to, Young's modulus, impact resistance (toughness), tensile strength, and tear strength. Impact resistance, or "toughness," is a measure of energy absorbed during fracture of a polymer sample of standard dimensions and geometry when subjected to very rapid impact loading. Toughness can be measured using Charpy and Izod impact tests to assess the brittleness of a material.

A plasticizer can be monomeric, polymeric, co-polymeric, or a combination thereof, and can be combined with a polymeric composition in the same manner as described above. Plasticization and solubility are analogous in the sense that selecting a plasticizer involves considerations similar to selecting a solvent such as, for example, polarity. Furthermore, plasticization can also be provided through covalent bonding by changing the molecular structure of the polymer through copolymerization.

Examples of plasticizing agents include, but are not limited to, low molecular weight polymers (such as single-block polymers, multi-block copolymers, and other copolymers such as graft copolymers), oligomers (such as ethyl-terminated oligomers of lactic acid), small organic molecules, hydrogen bond forming organic compounds with and without hydroxyl groups, polyols (such as low molecular weight polyols having aliphatic hydroxyls), alkanols (such as butanols, pentanols and hexanols), sugar alcohols and anhydrides of sugar alcohols, polyethers (such as poly(alkylene glycols)), esters (such as citrates, phthalates, sebacates and adipates), polyesters, aliphatic acids, proteins (such as animal proteins and vegetable proteins), oils (such as, for example, the vegetable oils and animal oils), silicones, acetylated monoglycerides, amides, acetamides, sulfoxides, sulfones, pyrrolidones oxa acids, diglycolic acids, and any analogs, derivatives, copolymers and combinations of the foregoing.

The amount of plasticizer used in the present invention, can range from about 0.001% to about 70%; from about 0.1% to about 50%; from about 0.6% to about 30%; from about 0.75% to about 25%; from about 1.0% to about 10%; and any range therein, as a weight percentage based on the total weight of the polymer and agent or combination of agents.

It should be appreciated that any one or any combination of the plasticizers described above can be used in the present invention. For example, the plasticizers can be combined to obtain the desired function. In some embodiments, a secondary plasticizer is combined with a primary plasticizer in an amount that ranges from about 0.001% to about 20%; from about 0.05% to about 10%; from about 1.0% to about 5%, or any range therein, as a weight percentage based on the total weight of the polymer, any agent or combination of agents in the coating layer.

Plasticizers may also be combined with other agents to obtain other desired functions such as, for example, an added therapeutic, prophylactic, and/or diagnostic function. In some embodiments, the plasticizers can be linked to other agents through ether, amide, ester, orthoester, anhydride, ketal, acetal, carbonate, and all-aromatic carbonate linkages.

Other Additives and Components of the Coating Compositions

The coating compositions and coating layers of the present invention may optionally further comprise one or more other additives or components. For example, the polymer matrix may be combined with ceramics and/or metals. Examples of ceramics include, but are not limited to, hydroxyapatite, BIO-GLASS®, and absorbable glass. Examples of metals include, but are not limited to magnesium, copper, titanium, and tantalum.

While particular embodiments of the present invention have been described, it will be obvious to those skilled in the art that changes and modifications can be made without departing from the spirit and scope of the teachings and embodiments of this invention. One skilled in the art will appreciate that such teachings are provided in the way of example only, and are not intended to limit the scope of the invention. Therefore, the appended claims are to encompass within their scope all such changes and modifications as fall within the true spirit of this invention.

The invention claimed is:

1. A method comprising:
preparing a coating composition comprising one or more polymers, one or more active agents, and one or more solvents;
applying the coating composition onto a surface of a medical device to form a wet coating layer;
rapidly cooling the wet coating layer to a temperature of −150° C. or lower by exposing the wet coating layer to a cold gas or a cold liquid;
wherein the morphology of the one or more active agents is fixed; and
after cooling the wet coating layer, removing solvent(s) to form a coating layer.

2. The method of claim 1 wherein after forming the coating layer the method comprises one or more post-formation process steps.

3. The method of claim 2 wherein the post-formation process steps are selected from the group consisting of annealing, applying a topcoat coating or barrier layer to a surface of the coating layer, applying a finishing coat layer, and sterilizing.

4. The method of claim 3, wherein the method comprises annealing the formed coating layer.

5. The method of claim 1 wherein the medical device is a stent.

6. The method of claim 1, wherein the wet coating layer is cooled to a temperature of −180° C. or less.

7. The method of claim 1, wherein the medical device comprises a primer layer, and the coating composition is applied to all or part of the primer layer.

8. The method of claim 3, wherein the method comprises applying a topcoat coating or barrier layer to a surface of the coating layer.

9. The method of claim 1 wherein the volume fraction of the one or more active agents to the one or more polymers in the coating layer is about 35% or greater.

10. The method of claim 1 wherein the volume fraction of the one or more active agents to the one or more polymers in the coating layer is about 25% or greater.

11. The method of claim 1 wherein the volume fraction of the one or more active agents to the one or more polymers in the coating layer is about 10% or greater.

12. The method of claim 1 wherein the one or more active agents comprise from about 0.02% to about 40% by weight of the total weight of the coating composition.

13. The method of claim 1 wherein the one or more active agents are selected from the group consisting of antiproliferative, antineoplastic, anti-inflammatory, steroidal anti-inflammatory, non-steroidal anti-inflammatory, antiplatelet, anticoagulant, antifibrin, antithrombin, antimitotic, antibiotic, antiallergic, antioxidant, and cytostatic agents, and combinations thereof.

14. The method of claim 1 wherein the one or more polymers are selected from the group consisting of poly(acrylates), acrylic polymers and copolymers, poly(cyanoacrylates), fluorinated polymers or copolymers, polycaprolactones, polylactides, poly(D-lactides), poly(L-lactides), poly(D,L-lactides), Poly(lactic acids), poly(glycolic acid), poly(lactide-co-glycolide)s, poly(glycolic acid-co-trimethylene carbonate)s, poly(lactic acid-co-trimethylene carbonate), poly(amino acids), polyhydroxyalkanoates, poly(hydroxyvalerates), polyhydroxybutyrates, poly(hydroxybutyrate-co-valerate)s, polymers and copolymers of hydroxyl ethyl methacryate, polydioxanones, polyorthoesters, polyanhydrides, polyphosphoesters, polyphosphoester urethanes, polyphosphazenes, polycarbonates, polyiminocarbonates, polytrimethylene carbonates, co-poly(ether-esters), poly(alkylene oxalates), polyurethanes, silicones, polyesters, polyolefins, poly(isobutylene) and ethylene-alphaolefin copolymers, vinyl halide polymers and copolymers, polyvinyl ethers, polyvinylidene halides, polyacrylonitrile, polyvinyl ketones, polyvinyl aromatics, polyvinyl esters, polyvinyl acetate, copolymers of vinyl monomers with each other and olefins, ethylene vinyl alcohol copolymers, polyamides, alkyd resins, polyoxymethylenes, polyimides, polyester amides, polyethers, poly(alkylene glycols), poly(tyrosine derived carbonates), poly(tyrosine derived arylates), epoxy resins, rayon, rayon-triacetate, biomolecules, poly(N-acetylglucosamine), chitosan, cellulose, cellulose acetate, cellulose butyrate, cellulose acetate butyrate, cellulose nitrate, cellulose propionate, cellulose ethers, carboxymethyl-cellulose, and copolymers and combinations thereof.

15. The method of claim 1 wherein the one or more solvents comprise from about 19.8% to about 99.8% by weight of the total weight of the coating composition.

16. The method of claim 1, wherein the active agent or at least one of the active agents is selected from the group consisting of dactinomycin, actinomycin IV, actinomycin $I_1$, actinomycin $X_1$, actinomycin $C_1$, paclitaxel, docetaxel, methotrexate, azathioprine, vincristine, vinblastine, fluorouracil, doxorubicin hydrochloride, mutamycin, adriamycin and mitomycin.

17. The method of claim 1, wherein the active agent or at least one of the active agents is selected from the group consisting of heparin, sodium heparin, heparin sulfate, hirudin, argatroban, forskolin, vapiprost, prostacyclin, dextran, D-phe-pro-arg-chloromethylketone (synthetic antithrombin), dipyridamole, and bivalirudin.

18. The method of claim 1, wherein the active agent or at least one of the active agents is selected from the group consisting of captopril, cilazapril, lisinopril, nifedipine, colchicine, nitroprusside, suramin, triazolopyrimidine, and permirolast potassium.

19. The method of claim 1, wherein the active agent or at least one of the active agents is selected from the group consisting of tacrolimus, dexamethasone, rapamycin, everolimus, 40-O-(3-hydroxyl)propyl-rapamycin, 40-O-[2-(2-hydroxyl)ethoxy]-ethyl-rapamycin, and 40-O-tetrazole-rapamycin.

* * * * *